US009092555B2

(12) United States Patent
Gunaratnam et al.

(10) Patent No.: US 9,092,555 B2
(45) Date of Patent: Jul. 28, 2015

(54) PATIENT ACTIVITY ALERT TOOL

(71) Applicant: ORACLE INTERNATIONAL CORPORATION, Redwood Shores, CA (US)

(72) Inventors: Vasanthan Gunaratnam, San Jose, CA (US); Stuart Costley, Arvada, CO (US); Divya Shah, Sunnyvale, CA (US); Alex Tam, San Francisco, CA (US); Philip Foeckler, Richmond, CA (US)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 85 days.

(21) Appl. No.: 13/955,098

(22) Filed: Jul. 31, 2013

(65) Prior Publication Data

US 2015/0035675 A1    Feb. 5, 2015

(51) Int. Cl.
*A61B 5/00* (2006.01)
*G06F 19/00* (2011.01)
*G08B 21/04* (2006.01)
*G08B 21/02* (2006.01)

(52) U.S. Cl.
CPC ........ *G06F 19/3418* (2013.01); *G08B 21/0453* (2013.01); *G08B 21/02* (2013.01)

(58) Field of Classification Search
CPC .............. G08B 21/182; G08B 21/0453; G06F 19/3418
USPC .............. 340/539.12, 573.1, 573.4, 506, 517, 340/562; 600/300, 301, 309, 483, 484, 544; 128/903, 904
See application file for complete search history.

(56) References Cited

U.S. PATENT DOCUMENTS

| 5,348,008 | A  | * | 9/1994 | Bornn et al.   | 600/301 |
| 7,319,386 | B2 | * | 1/2008 | Collins et al. | 340/539.12 |
| 7,656,299 | B2 | * | 2/2010 | Gentry et al.  | 340/573.1 |
| 2011/0201944 | A1 | * | 8/2011 | Higgins et al. | 600/483 |
| 2012/0203078 | A1 | * | 8/2012 | Sze et al.     | 600/301 |
| 2014/0022080 | A1 | * | 1/2014 | Mayoras, Jr.   | 340/573.1 |
| 2014/0152436 | A1 | * | 6/2014 | Langer         | 340/539.12 |

* cited by examiner

*Primary Examiner* — Van Trieu
(74) *Attorney, Agent, or Firm* — Kraguljac Law Group, LLC

(57) ABSTRACT

Systems, methods, and other embodiments associated with a patient activity alert tool are described. In one embodiment, a system includes a risk notification logic configured to receive a risk notification from a patient. The risk notification includes a threshold condition. The threshold condition may be a time interval during which the patient is at increased risk to experience an adverse event. The example system also includes a threshold logic configured to determine that the threshold condition has been met without receipt of a clearance notification from the patient. The threshold logic then generates an alert. An alert logic sends the alert to a caregiver selected by the patient.

18 Claims, 10 Drawing Sheets

US 9,092,555 B2

PATIENT ACTIVITY ALERT TOOL

BACKGROUND

When a patient experiences adverse effects (e.g., symptoms, reactions, side effects) of a health condition (e.g., disease, syndrome, or allergy), the patient contacts medical services. This may be difficult based on the severity of the adverse affects. Even if the patient is able to contact emergency medical services, the patient may not get through if the telephone lines are busy, the patient is put on hold, or the institution is closed. Once the patient reaches emergency medical services, the patient then has to convey what has happened, the patient's health condition, the patient's location, and so on. Again this may be difficult based on the severity of the adverse effect that the patient is suffering. Moreover, it wastes time that may be crucial to the patient's recovery.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
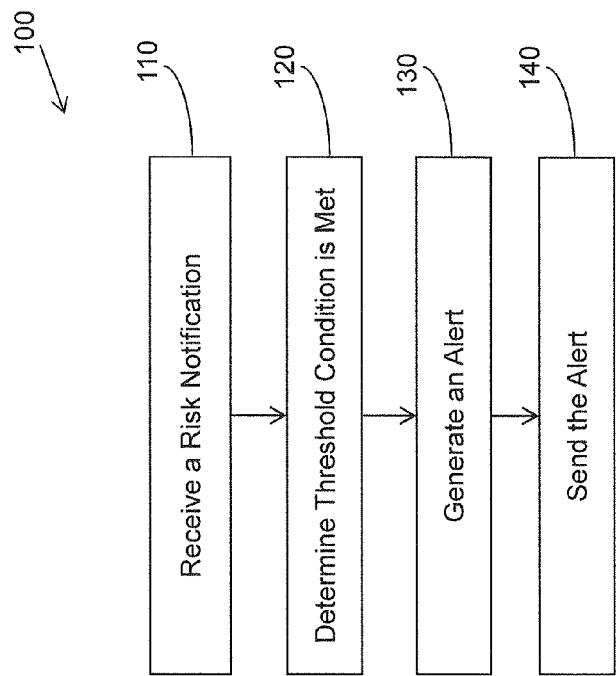
FIG. 1 illustrates one embodiment of a method associated with a patient activity alert tool.

Many people suffer from chronic conditions that make them susceptible to health related adverse events. For example, people with epilepsy are at risk of seizures and people with diabetes may experience dizziness. These conditions make it difficult to pursue independent activities such as exercise and performing errands that take a person outside their home.

"Patient," as referred herein, describes a person that is an increased risk to suffer from an adverse event. The adverse event may be related to a chronic illness (e.g., epilepsy, diabetes) that the patient suffers from. The adverse event may be related to environmental factors. For example, a patient may be concerned about the amount of time spent in polluted environment. The adverse event may be related to a social situation (e.g., being in a situation with strangers, or going to place the patient has not been before).

"Caregiver," as referred herein, describes a person that offers some form of support or care to the patient. The caregiver may be a medical professional monitoring the patient's health. Alternatively, the caregiver may be a social contact (e.g., friend, colleague, partner) or family member that offers care or supports the patient. The caregiver may also be a paid individual who monitors the patient for a fee.

Described herein are systems and methods for alerting a caregiver that offers some level of care to a patient that may experience adverse events such as seizures and dizziness. Before a patient takes part in an activity that may heighten the patient's risk of an adverse event, the patient may send a notification to notify the patient's caregiver of a change in the patient's status. The patient may turn off the alert mode when the patient is once more in a safe state, which would also be communicated to the caregiver. The alert mode gives the caregiver notice to monitor the patient, prepares the caregiver to take action, and provides the caregiver with contextual information to be able to take action.

A patient typically waits until he or she is suffering from the adverse effects of a health crisis before attempting to contact emergency medical services (e.g., emergency medical technicians, paramedics). Allowing a patient to alert a caregiver when the patient believes that he or she is at an increased risk to suffer from an adverse event alleviates the burden on the patient to attempt to get help while he or she is suffering. Instead, the patient could rely on a caregiver to contact emergency medical services if need be. Reaching out to a caregiver before an adverse event would also reduce the burden on the emergency medical services, since emergency medical services would have a capable point of contact in the caregiver. A patient reaching out before a possible adverse event would also reduce the stress on a caregiver who may be worried about the patient but not want to inundate the patient with messages to determine whether the patient is at an increased risk to suffer from an adverse event or the patient is in a safe state.

Figure 8:
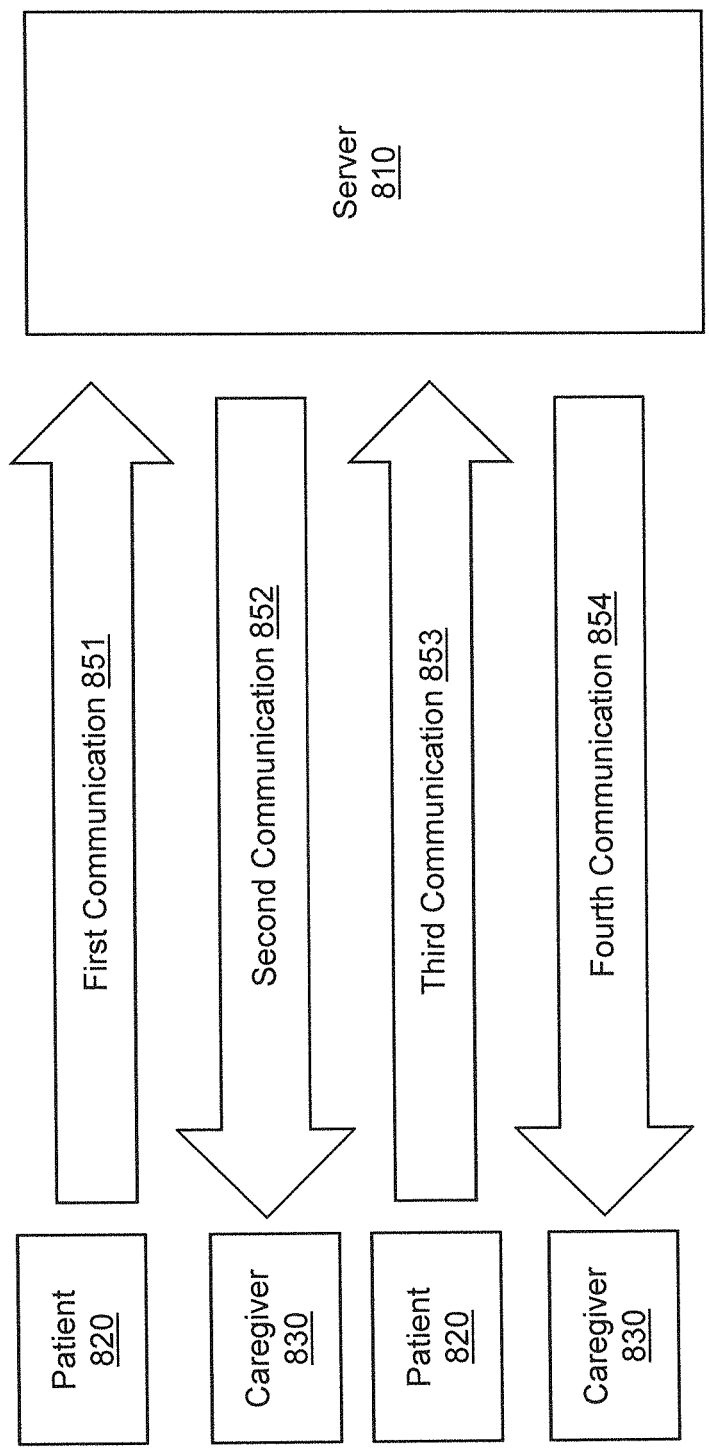
FIG. 8 illustrates one embodiment of communication in a system associated with a patient activity alert tool.

Systems and methods described herein provide a patient activity alert tool for alerting caregivers of a patient's activities. In one embodiment various aspects of the patient activity alert tool are implemented on a patient's electronic device, on a caregiver's electronic device, and/or on an optional server. The term "electronic device" encompasses mobile devices such as cell phones and digital assistants, computers, or any other device that includes a processor and is capable of communicating with another device. The patient activity alert tool provides a framework for a patient's electronic device to interact with a caregiver's electronic device to send an alert to a caregiver's electronic device when a patient may be experiencing an adverse event. FIG. 8 illustrates one embodiment in which a server is the intermediary between the patient's electronic device and the caregiver's electronic device. In this embodiment, which will be described in more detail below, the patient's electronic device and the caregiver's electronic device communicate with the server by way of the internet.

Using the tool on the patient's electronic device, the patient sends a risk notification to a caregiver's electronic device to let the caregiver know that the patient is at an increased risk to suffer from an adverse event. The risk notification includes a threshold condition that specifies a set of circumstances in which a caregiver should be alerted that the patient may be experiencing an adverse event. Example threshold conditions include elevated heart rate, low blood oxygen, a sustained interval of aerobic activity, or a time interval. If the threshold condition is met, an alert is generated and sent to the caregiver so that the caregiver is aware of a possible problem.

FIG. 1 illustrates one embodiment of a method associated with a patient activity alert tool. The method described in FIG. 1 includes actions that are performed by the caregiver's electronic device. At 110, a risk notification is received by the caregiver's device from a patient's electronic device. The risk notification indicates that the patient is at an increased risk to experience an adverse event. The risk notification includes a threshold condition. The threshold condition may be selected based on activity factors such as the patient's health (e.g., heart rate, breathing), distance traveled from a starting point, or a time interval. The threshold condition may be monitored by a mobile device that has monitoring capability (e.g., heart rate monitoring, GPS location services, timing circuitry). The risk notification may also include contextual data, such as the activity (e.g., walking, running, swimming, hiking, sport) that the patient is participating in, a location or planned route of the activity, or whether the patient is accompanied.

For example, if the patient is at an increased risk to suffer from a seizure when participating in aerobic activity, the patient may use the patient activity alert tool on the patient's electronic device to send a risk notification when going for a run. The risk notification may include a threshold condition that is a time interval and planned route of the run. The time interval may correspond to the length of time that the patient is planning to participate in the aerobic activity. Alternatively, the time interval may be based on a different metric, such as how long the patient has, or expects to have, an elevated heart rate. In another example the threshold condition may be a predetermined heart rate of a specified beats per minute.

At 120, it is determined whether the threshold condition has been met without the receipt of a clearance notification from the patient's electronic device. A clearance notification indicates that the patient is no longer subject to an increased risk of experiencing an adverse event. The caregiver's electronic device may receive a clearance notification sent manually by the patient from the patient's electronic device or the clearance notification may be sent in response to a clearance condition being met. For example, if the patient is going for a run, the clearance condition may be the patient recovering to a heart rate of a specified beats per minute. Alternatively, reaching a predetermined point or returning to the starting point may satisfy the clearance condition. More than one clearance condition may be used. For example, the clearance condition may be satisfied when the patient's heart rate recovers to a specified beats per minute and/or reaching a specific location.

If the threshold condition is met without receiving a clearance notification from the patient, at 130, an alert is generated. At 140, the alert is sent to the caregiver's electronic device. The alert informs a caregiver that the threshold condition has been met without receiving a clearance notification from the patient. The alert may include the contextual data such as care instructions (e.g., contact emergency services, administer specified amount of medication). The alert may also include response options that provide a mode for the caregiver to respond to the alert. For example, the alert may include a quick call option that allows a caregiver to make a call for aid using a single button. Alternatively, the quick call option may allow the caregiver to call the patient using a single button.

The alert may be repeated if the caregiver does not take action. In one embodiment, the alert is set to repeat every ten minutes for sixty minutes unless the caregiver takes action. The action may include acknowledging the alert on the caregiver's electronic device or selecting a quick call option to call the patient's electronic device. The alert may be repeated with increasing or decreasing frequency.

While the systems and methods herein have been described with respect to a patient subject to a medical risk, the systems methods are applicable in many fields. For example, a person travelling to the home of a stranger to buy an item could use the patient activity alert tool to send a risk notification to electronic devices of social contacts indicating that buying the item should take a predetermined amount of time (e.g., half-hour). Therefore, setting the threshold condition as a time interval of thirty minutes. If a clearance notification is not sent by the buyer within the pre-determined amount of time, the social contacts are sent an alert.

Figure 2A:
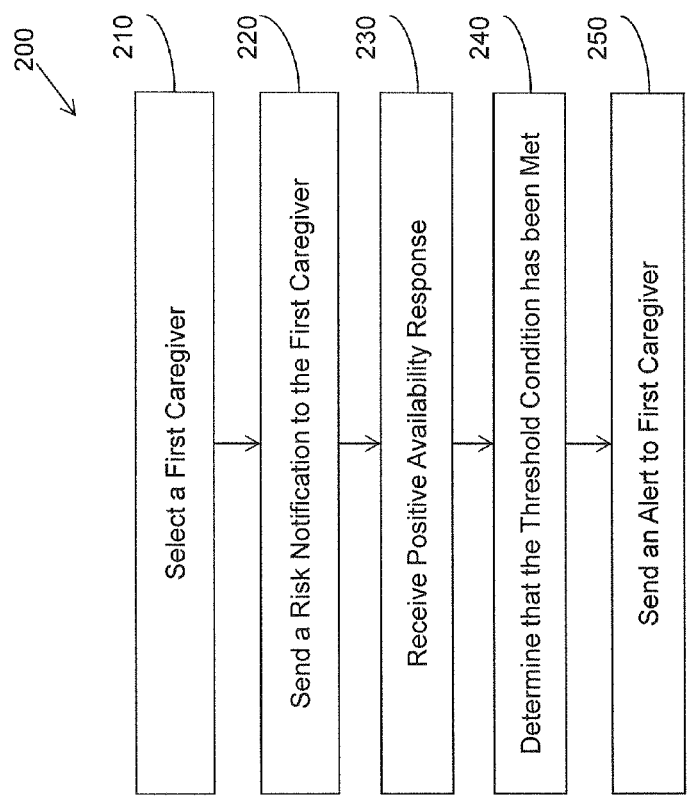
FIG. 2A illustrates another embodiment of a method associated with a patient activity alert tool.

FIG. 2A illustrates one embodiment of a method 200 associated with a patient activity alert tool. The method described in FIG. 2A includes steps that are performed by the patient's electronic device. Method 200 includes, at 210, selecting a first caregiver. The caregivers may be selected from social networking groups of social networking websites, such as, FACEBOOK®, LINKEDIN®, or MEETUP®. Caregivers may be selected based on their availability online. The patient may also add to the group of caregivers by providing contact information, like email addresses or mobile telephone numbers.

At 220, the first caregiver's electronic device is sent a risk notification indicating that the patient is at an increased risk to suffer an adverse event. The threshold condition defines certain circumstances in which the caregiver should receive alerts. In this example, the threshold condition is a time interval. The time interval indicates the length of time that the patient will be subject to the increased risk. The first caregiver's electronic device sends a first availability response that specifies whether the first caregiver is available during the time interval. In one embodiment, the risk notification is sent to a plurality of caregivers' electronic devices. At 230, a positive availability response is received stating that the caregiver is available. At 240, it is determined that the threshold condition has been met (e.g., that the time interval has expired) without receiving a clearance notification from the patient. In response to the threshold condition being met, at 250, an alert is sent to the first caregiver's electronic device.

Figure 2B:
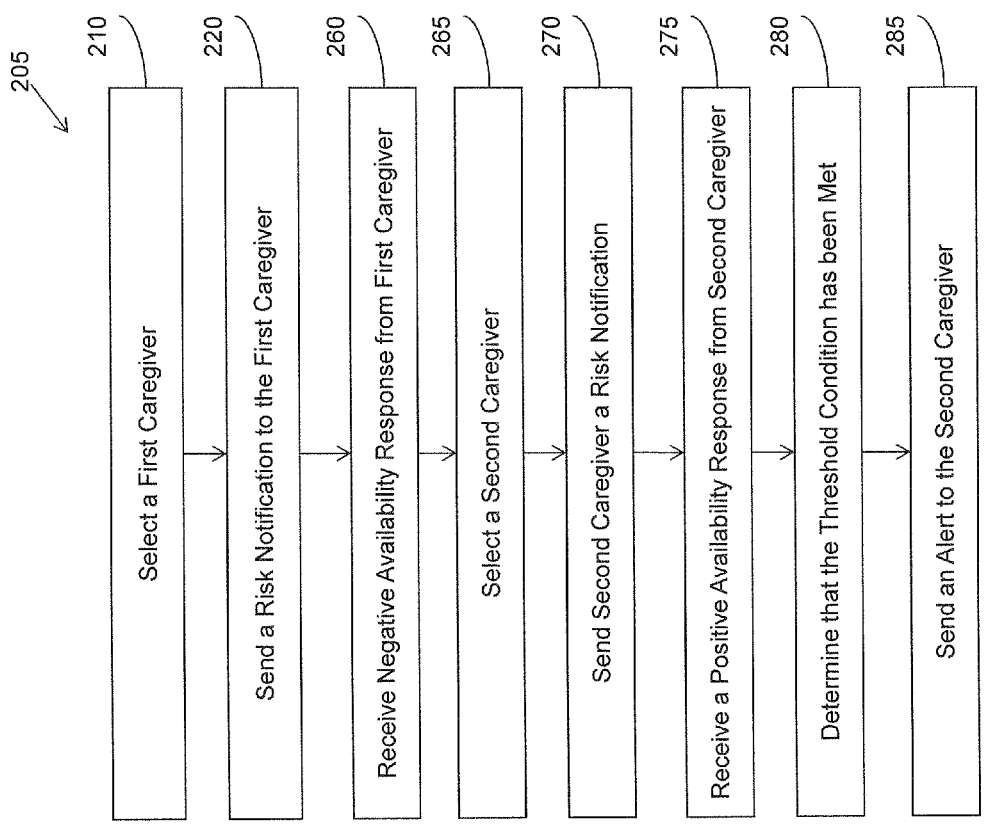
FIG. 2B illustrates another embodiment of a method associated with a patient activity alert tool.

FIG. 2B illustrates one embodiment of a method 205 associated with a patient activity alert tool. The method described in FIG. 2 includes steps that are performed by the patient's electronic device. Method 205 includes similar elements as method 200 of FIG. 2A but includes steps that are performed if the first caregiver is unavailable. At 210, a first caregiver is selected from the group of caregivers, and, at 220, the first caregiver's electronic device is sent a risk notification having a threshold condition.

At 260, a negative availability response is received by the patient's electronic device stating that the first caregiver is not available. At 265, the patient selects a second caregiver. In one embodiment, the patient compiles a list of caregivers and a next caregiver on the list is selected when a given caregiver is unavailable. At 270, a risk notification including a threshold condition is sent to the second caregiver's electronic device. At 275, a positive availability response is received from the second caregiver's electronic device indicating that the second caregiver is available. At 280, it is determined that the threshold condition has been met without receiving a clearance notification from the patient. In response to the threshold condition being met without receipt of a clearance notification, at 285, an alert is sent to the second caregiver's electronic device. An alert is not sent to the first caregiver.

Figure 3:
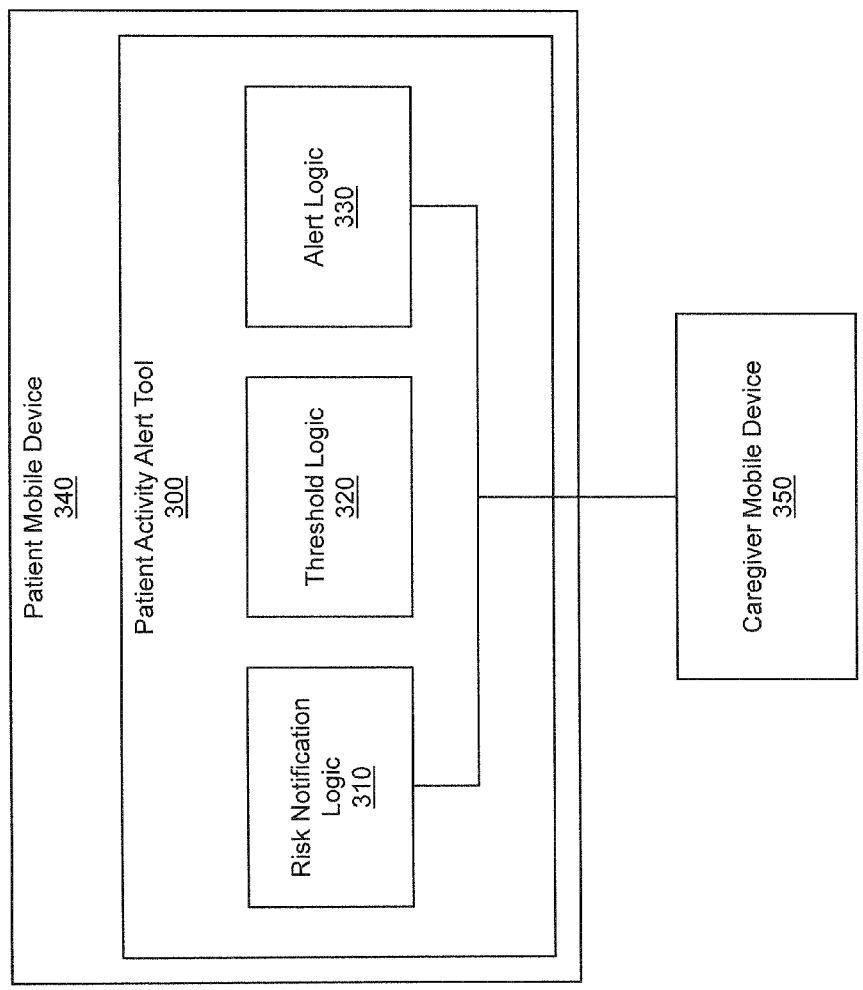
FIG. 3 illustrates one embodiment of a system associated with a patient activity alert tool.

FIG. 3 illustrates one embodiment of a patient activity alert tool 300 implemented on a patient's mobile device 340. The patient activity alert tool 300 may be run as software in execution on a computer, an application on the mobile device, or may be launched as an applet from a web page. The patient activity alert tool 300 includes a risk notification logic 310, a threshold logic 320, and an alert logic 330. In this embodiment, the patient activity alert tool 300 is configured in a patient's mobile device 340, but the patient activity alert tool 300 may be implemented on any computing device.

When activated by a patient, the risk notification logic 310 generates a risk notification. The risk notification logic 310 receives, from the patient, caregiver data and contextual data regarding an elevated risk that the patient is subject to. The caregiver data specifies a caregiver including contact information. The contextual data includes data about the cause or consequences of the elevated risk, descriptive data about the patient's activity (e.g., length of time, location, list of other participants), and details about the patient's health. The contextual data may include additional information that the patient deems relevant. The risk notification logic 310 uses the caregiver data and the contextual data to generate a risk notification (e.g., an electronic message or notice). The risk notification is sent via a communications network to one or more destinations (e.g., mobile device 350 of the caregiver) identified by the caregiver data.

The threshold logic 320 receives a threshold condition, that when met, will cause an alert to be sent to the caregiver. The threshold logic 320 monitors the threshold condition to determine if the threshold condition has been met. When the threshold condition is met, a trigger is sent to the alert logic 330. The alert logic 330 generates an alert using the caregiver data and contextual data received by the risk notification logic 310. The alert logic 330 may include instructions from the patient that convey medical issues to be addressed, possible treatment options, or medical personnel to be contacted in the alert. The alert is sent to mobile device 350 of the caregiver identified by the caregiver data.

Figure 4D:
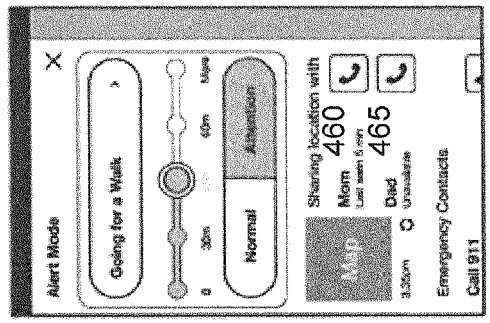
FIGS. 4A-4D illustrate, for one embodiment of a patient activity alert tool, a series of example screen shots used by a patient to initiate alert mode.
Figure 4C:
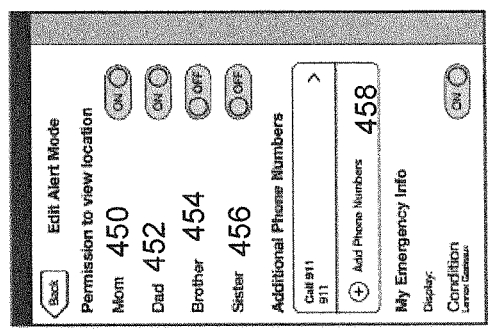
Figure 4B:
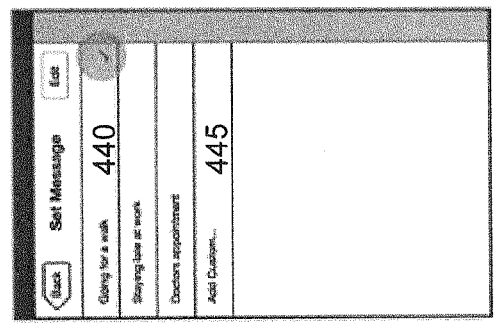
Figure 4A:
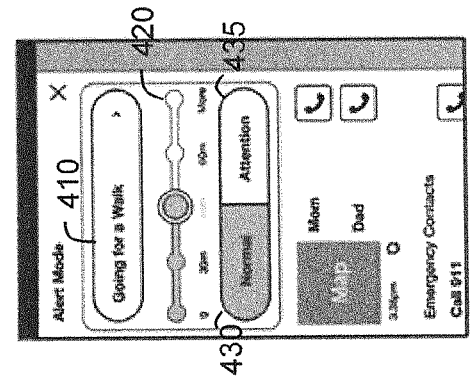

FIGS. 4A-4D illustrate one example of a patient activity alert tool application in use on a patient's mobile device. FIG. 4A illustrates an example screen shot of one embodiment of a patient activity alert tool. This screen interface allows a patient to setup a risk notification. The patient is provided with an activity menu 410 in which the patient has selected "going for a walk." In this example, the threshold condition is a time interval indicative of the duration of the activity. The time interval of the activity can be selected on a sliding scale 420. The patient may select to make this activity "normal" 430 or "attention" 435. Normal 430 is selected if the patient is logging this activity for the patient's own records. Attention 435 is selected if the patient is going to send caregivers a risk notification.

Selecting Attention 435 causes the patient activity alert tool to enter alert mode. Consequently, the patient activity alert tool will exit a passive "normal" state. In another embodiment, Attention 435 may be selected automatically when an alert mode threshold condition is met so that the patient activity alert tool will enter alert mode. For example, the patient activity alert tool may be linked to a heart rate monitor. If the patient's heart rate exceeds the alert mode threshold condition, the alert mode may be automatically activated. The alert mode threshold condition that causes the alert mode to be automatically activated may be different than a threshold condition that causes an alert to be generated.

FIG. 4B illustrates an example screen shot of one embodiment of a patient activity alert tool. This screen illustrates a menu of activity options that is displayed by selecting the activity menu 410 (as shown in FIG. 4A). The activity options are provided by the patient activity alert tool. Activity options may be remotely stored in an activity database that the patient activity alert tool has access to. Here, the activity "Going for a walk" 440 is selected. The patient may alternatively select "Add Custom" 445 to add an activity that the patient is likely to perform that is not already in the activity database.

FIG. 4C illustrates an example screen shot of one embodiment of a patient activity alert tool. The patient activity alert tool displays a group of caregivers associated with the patient, such as Mom 450, Dad 452, Brother 454, and Sister 456. The caregivers may be stored in a caregiver database. In one embodiment, the activity alert tool may display the availability of individual caregivers in the group.

The caregivers are selected using a toggle switch. For example, Mom 450 and Dad 452 are both selected to be "on." Therefore, Mom 450 and Dad 452 are selected to receive notifications and alerts. Brother 454 and Sister 456 are selected to be "off," and therefore, Brother 454 and Sister 456 will not receive notifications and alerts. The patient may additionally or alternatively select "Add Phone Numbers" 458 to add the contact information of a caregiver that is not already stored in the caregiver database.

FIG. 4D illustrates an example screen shot of one embodiment of a patient activity alert tool. Once the caregivers have been selected (as shown in FIG. 4C), the patient activity alert tool anticipates the availability of caregivers. Here "Mom" 460 is shown as having been seen in the last five minutes and "Dad" 465 is unavailable. Availability may be determined by messaging between the patient and the caregiver. Alternatively, the patient activity alert tool may monitor the caregivers' access to a wireless network and display that information. In one embodiment, if the caregiver is actively online and using a patient activity alert tool, the caregiver may be shown as available. If the caregiver is not using a patient activity alert tool the caregiver may be shown as unavailable. The patient activity alert tool may be able to gauge the length of time that a caregiver has been inactive with the patient activity alert tool still on, and relate the determined amount of time to the patient as that caregiver being "last seen" that determined amount of time ago.

The patient activity alert tool may also provide input methods to enter contextual data. For example, the patient adds information regarding a medical condition the patient suffers from. Depending on the medical condition, the patient activity alert tool includes additional information, such as "Seizure Type" and "Medication" that the patient is taking. The patient may also a use a text box to enter special instructions to be sent to a caregiver in an alert if necessary.

FIGS. 4A-4D illustrate one embodiment of a patient activity alert tool. However, the functionality of the patient activity alert tool may be implemented any number of ways. For example, drop down menus and toggle switches are illustrated, however, the patient activity alert tool may be implemented with different menus (e.g., context menu, pie menu, list menu, dialog box) or different buttons (e.g., radio buttons, check boxes, cycle button, slider button).

Figures 5A, 5B:
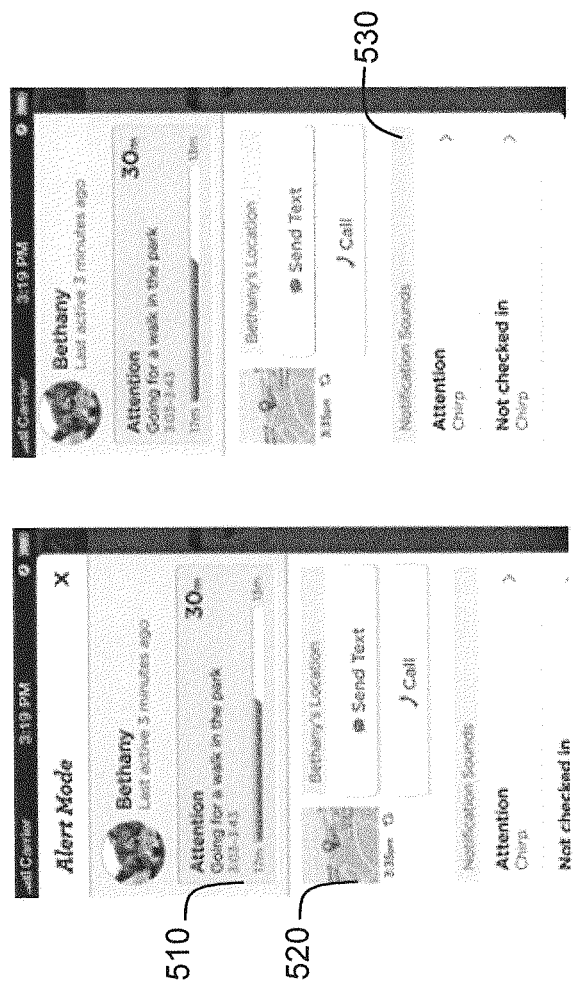
FIGS. 5A-5B illustrate, for one embodiment of a patient activity alert tool, example screen shots used by a caregiver to monitor a patient.

FIGS. 5A-5B illustrate one example of a patient activity alert tool application in use on a caregiver's mobile device. FIG. 5A illustrates a screen, displayed to a caregiver, that shows a patient's progress 510 with respect to the time interval. In the example shown, a patient identified as "Bethany" is in an alert mode for 30 minutes as she goes for a walk in the park. Contextual data in the form of a map 520 illustrates her location as of a given time.

FIG. 5B illustrates an example screen shot of one embodiment of a patient activity alert tool. This screen provides an interface for a caregiver to set notification sounds 530 when the patient sets an alert mode with the caregiver selected. The caregiver can also select notification sounds 530 in the event that the patient has not checked in before the time interval elapses.

Figure 6B:
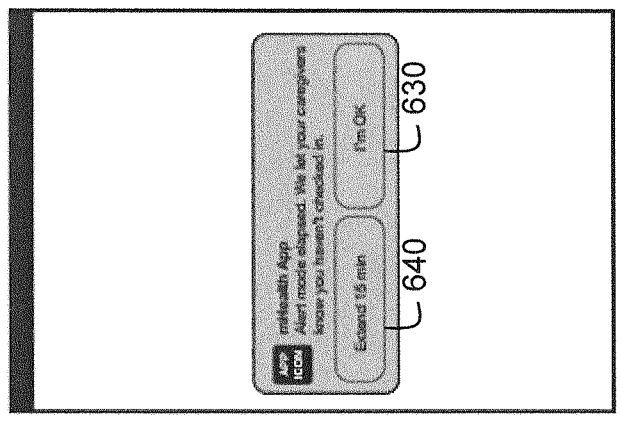
FIGS. 6A-6B illustrate, for one embodiment of a patient activity alert tool, example screen shots that provide notifications to a patient when a threshold condition is met.
Figure 6A:
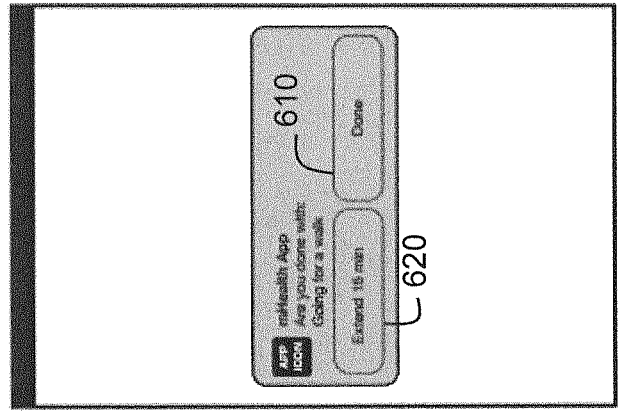

FIGS. 6A-6B illustrate one example of a patient activity alert tool application in use on a patient's mobile device. FIG. 6A illustrates an example screen shot that tracks the duration of the time interval in alert mode. When the time interval ends, the patient is prompted by the patient activity alert tool to determine whether the patient has completed the activity. In one embodiment, the patient is prompted to select "done" 610 to indicate that the activity has ended or select "Extend 15 min" 620 to extend the time interval before the time interval elapses.

Extending the time interval affords the patient additional time to respond before the time interval elapses. In the example illustrated, Extend 15 min 620 extends the time interval by 15 minutes. The predetermined amount of time to extend the time interval may be set by the patient, pre-programmed in the patient activity alert tool, or a function of the length of the time interval selected for the activity.

FIG. 6B illustrates an example screen shot that notifies a patient that an alert has been sent to the caregiver. In the event that a patient does not indicate that the activity has ended (e.g., selection 610 in FIG. 6A) or extended the time interval (e.g., selection 620 in FIG. 6A) before the time interval elapses, an alert is sent. In one embodiment, the patient is given a predetermined time after the time interval elapses to respond prior to the sending of an alert to a caregiver. A dialog box informs the patient that an alert has been sent to the caregivers. The patient can end the alert by selecting "I'm OK" 630 or extend the elapsed time interval by selecting "Extend 15 min" 640. Regardless of the option chosen by the patient the caregiver will receive a notification to inform the caregiver of the choice.

Figure 7C:
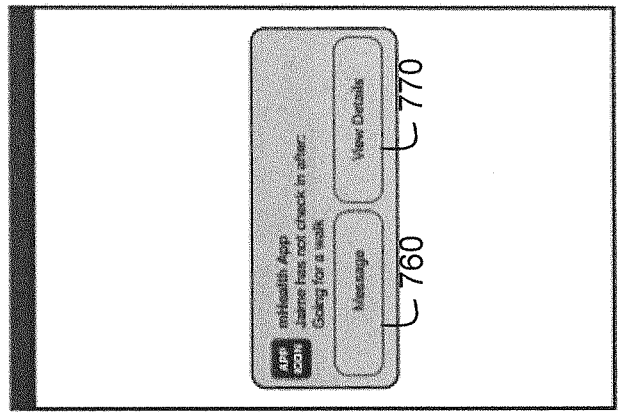
FIGS. 7A-7C illustrate, for one embodiment of a patient activity alert tool, example screen shots that provide notifications to a caregiver about a patient being monitored by the caregiver.
Figure 7B:
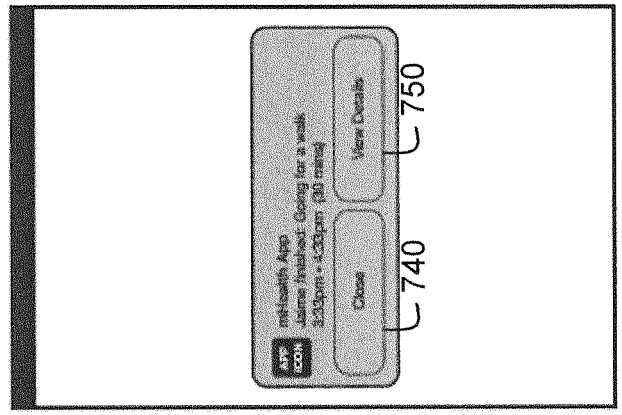
Figure 7A:
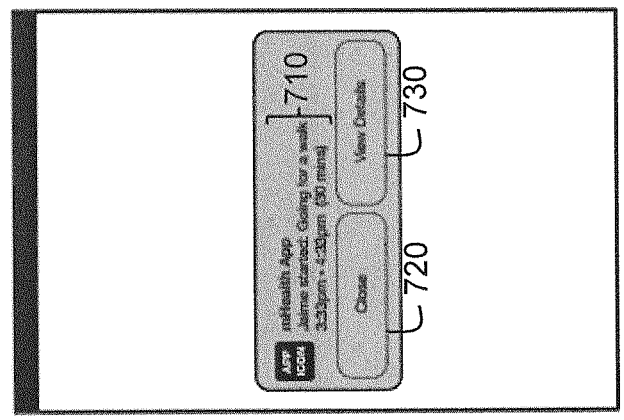

FIGS. 7A-7C illustrate one example of a patient activity alert tool application in use on a caregiver's mobile device. FIG. 7A illustrates an example screen shot that shows a risk notification received by a caregiver. The risk notification identifies details 710 of the risk including the patient, the activity the patient is participating in, and the time interval of the activity. The caregiver can close the risk notification by selecting "Close" 720. Alternatively, the caregiver may choose to view further contextual data by selecting "View Details" 730.

FIG. 7B illustrates an example screen shot that is displayed to the caregiver when the time interval elapses. The caregiver may close the notification by selecting "Close" 740 or opt to review details of the activity by selecting "View Details" 750.

FIG. 7C illustrates an example screen shot that is displayed to the caregiver in the event that the patient does check in by sending a clearance notification. The alert provides response options to respond to the alert. In one embodiment, the alert allows the caregiver to message the patient by selecting "Message" 760. The alert may also provide a quick call option (not shown) allowing the caregiver to contact other caregivers or medical personnel by selecting a different button. Alternatively, the caregiver may choose to view further contextual data by selecting "View Details" 770.

FIG. 8 illustrates one embodiment of communication in a system associated with a patient activity alert tool. The communication performed during operation of a patient activity alert tool is between a server 810, a patient's electronic device 820, and a caregiver's electronic device 830. In a first communication 851, a threshold condition associated with the patient's electronic device 820 is communicated to the server 810. The threshold condition specifies a set of circumstances in which the caregiver's electronic device 830 should be alerted that the patient 820 may be experiencing an adverse event. The first communication 851 may be manually sent by the patient interacting with the patient's electronic device 820. In a second communication 852, the server 810 forwards the risk notification to the caregiver's electronic device 830.

In one embodiment, the server evaluates the threshold condition using data received from the patient's electronic device 820. If the patient returns to a safe state before the threshold condition is met, a third communication 853 including a clearance notification is sent by the patient's electronic device 820 to the server 810. The patient may manually interact with the patient's electronic device 820 to send the third communication 853. Alternatively, the patient's electronic device 820 may automatically detect that the patient is safe (e.g., heart rate returned to normal or patient returning home) and automatically send the third communication 853 to the server 810. In fourth communication 854 the server 810 sends a message to the caregiver's electronic device 830 that the patient has returned to a safe state.

The communication outlined in FIG. 8 uses the server 810 as an intermediary between the patient's electronic device 820 and caregiver's electronic device 830, rather than having the patient's electronic device 820 communicate directly with the caregiver's electronic device 830. Using a server 810 to communicate between the patient's electronic device 820 and the caregiver's electronic device 830 avoids problems that may be caused by direct communication between the patient's electronic device 820 and the caregiver's electronic device 830. For example, regardless of whether the patient is out of range of a network when the threshold condition is met (e.g., the time interval elapses), the server 810 will send an alert to the caregiver's electronic device 830.

In this manner, the patient can let a caregiver know that the patient is at an increased risk to suffer from an adverse event. The caregiver can then prepare to take an action if need be. Conversely, a caregiver does not have to constantly check in with a patient to determine if the patient is not experiencing an adverse event.

Figure 9:
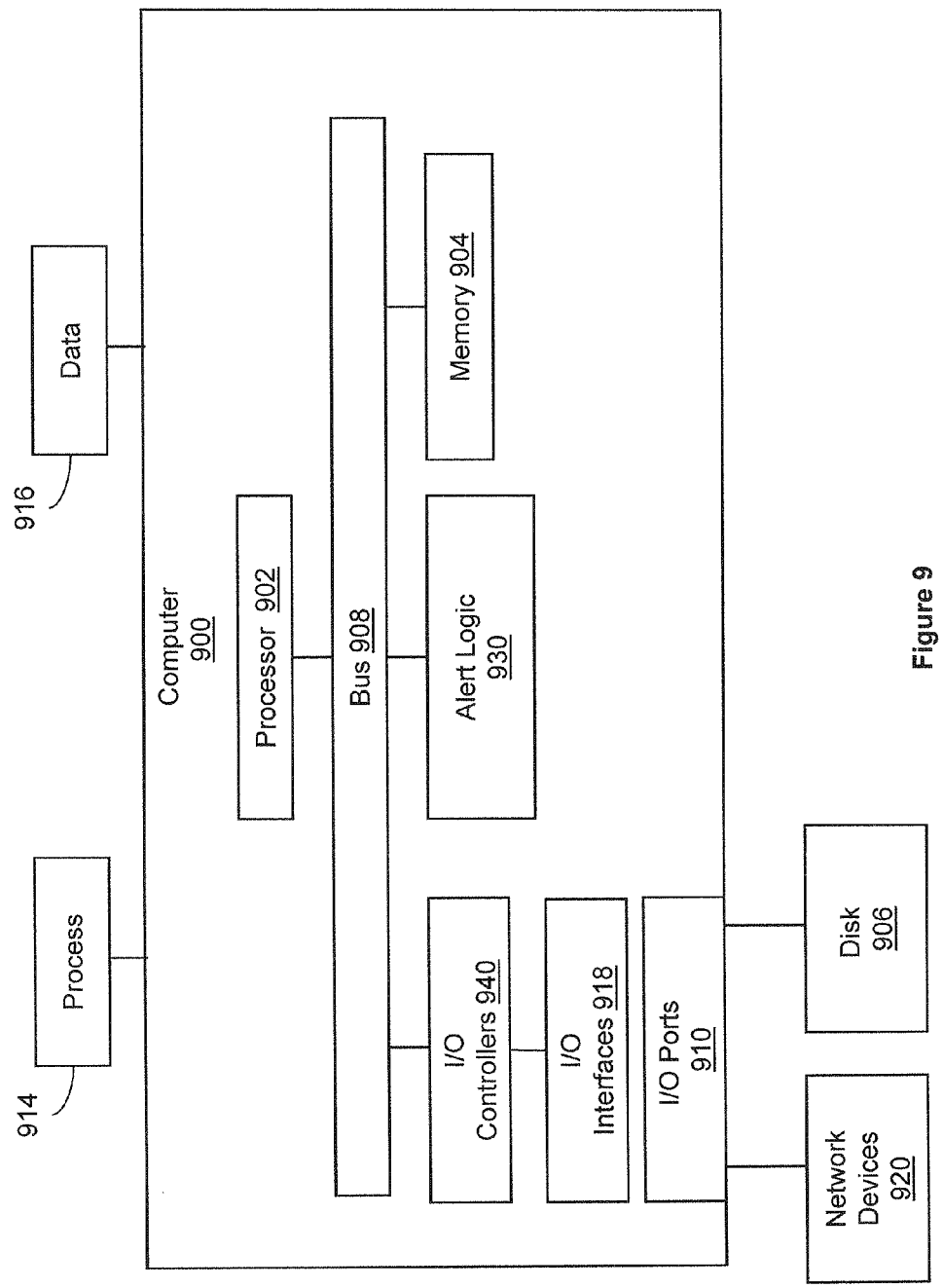
FIG. 9 illustrates an embodiment of a computing system in which example systems and methods, and equivalents, may be implemented.

FIG. 9 illustrates an example computing device that is configured and/or programmed with one or more of the example systems and methods described herein, and/or equivalents. The example computing device may be a computer 900 that includes a processor 902, a memory 904, and input/output ports 910 operably connected by a bus 908. In one example, the computer 900 may include patient activity alert logic 930 configured to facilitate sending risk notifications and alerts to a caregiver. The patient activity alert logic 930 is further configured to send an alert when it is determined that a threshold condition has been reached. The threshold condition may be marked by a time interval elapsing. In different examples, the logic 930 may be implemented in hardware, a non-transitory computer-readable medium with stored instructions, firmware, and/or combinations thereof. While the logic 930 is illustrated as a hardware component attached to the bus 908, it is to be appreciated that in one example, the logic 930 could be implemented in the processor 902.

In one embodiment, logic 930 or the computer is a means (e.g., hardware, non-transitory computer-readable medium, firmware) for selecting at least one caregiver to receive a risk notification and receive an availability response from at least one caregiver. The logic 930 is a means for receiving both caregiver data and contextual data. The means may be implemented, for example, as an ASIC programmed to perform these operations. The means may also be implemented as stored computer executable instructions that are presented to computer 900 as data 916 that are temporarily stored in memory 904 and then executed by processor 902. The computer executable instructions may include instructions for performing the methods outlined with respect to FIGS. 1, 2A, and/or 2B.

Logic 930 may also provide means (e.g., hardware, non-transitory computer-readable medium that stores executable instructions, firmware) for generating an alert in response to a threshold condition being met without receiving a clearance notification.

Generally describing an example configuration of the computer 900, the processor 902 may be a variety of various processors including dual microprocessor and other multi-processor architectures. A memory 904 may include volatile memory and/or non-volatile memory. Non-volatile memory may include, for example, ROM, PROM, and so on. Volatile memory may include, for example, RAM, SRAM, DRAM, and so on.

A disk 906 may be operably connected to the computer 900 via, for example, an input/output interface (e.g., card, device) 918 and an input/output port 910. The disk 906 may be, for example, a magnetic disk drive, a solid state disk drive, a floppy disk drive, a tape drive, a Zip drive, a flash memory card, a memory stick, and so on. Furthermore, the disk 906 may be a CD-ROM drive, a CD-R drive, a CD-RW drive, a DVD ROM, and so on. The memory 904 can store a process 914 and/or a data 916, for example. The disk 906 and/or the memory 904 can store an operating system that controls and allocates resources of the computer 900.

The bus 908 may be a single internal bus interconnect architecture and/or other bus or mesh architectures. While a single bus is illustrated, it is to be appreciated that the computer 900 may communicate with various devices, logics, and peripherals using other busses (e.g., PCIE, 1394, USB, Ethernet). The bus 908 can be types including, for example, a memory bus, a memory controller, a peripheral bus, an external bus, a crossbar switch, and/or a local bus.

The computer 900 may interact with input/output devices via the i/o interfaces 918 and the input/output ports 910. Input/output devices may be, for example, a keyboard, a microphone, a pointing and selection device, cameras, video cards, displays, the disk 906, the network devices 920, and so on. The input/output ports 910 may include, for example, serial ports, parallel ports, and USB ports.

The computer 900 can operate in a network environment and thus may be connected to the network devices 920 via the i/o interfaces 918, and/or the i/o ports 910. Through the network devices 920, the computer 900 may interact with a network. Through the network, the computer 900 may be logically connected to remote computers. Networks with which the computer 900 may interact include, but are not limited to, a LAN, a WAN, and other networks.

In another embodiment, the described methods and/or their equivalents may be implemented with computer executable instructions. Thus, in one embodiment, a non-transitory computer-readable medium is configured with stored computer executable instructions that when executed by a machine (e.g., processor, computer, and so on) cause the machine (and/or associated components) to perform the method.

While for purposes of simplicity of explanation, the illustrated methodologies in the figures are shown and described as a series of blocks, it is to be appreciated that the methodologies are not limited by the order of the blocks, as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional blocks that are not illustrated. The methods described herein are limited to statutory subject matter under 35 U.S.C §101.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer communication", as used herein, refers to a communication between computing devices (e.g., computer, personal digital assistant, cellular telephone) and can be, for example, a network transfer, a file transfer, an applet transfer, an email, an HTTP transfer, and so on. A computer communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, and so on.

"Computer-readable medium", as used herein, refers to a non-transitory medium that stores instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read. The computer-readable medium described herein are limited to statutory subject matter under 35 U.S.C §101.

"Logic", as used herein, includes a computer or electrical hardware component(s), firmware, a non-transitory computer readable medium that stores instructions, and/or combinations of these components configured to perform a function(s) or an action(s), and/or to cause a function or action from another logic, method, and/or system. Logic may include a microprocessor controlled by an algorithm, a discrete logic (e.g., ASIC), an analog circuit, a digital circuit, a programmed logic device, a memory device containing instructions that when executed perform an algorithm, and so on. Logic may include one or more gates, combinations of gates, or other circuit components. Where multiple logics are described, it may be possible to incorporate the multiple logics into one physical logic component. Similarly, where a single logic unit is described, it may be possible to distribute that single logic unit between multiple physical logic components. The logic described herein are limited to statutory subject matter under 35 U.S.C §101.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is used in the detailed description or claims (e.g., A or B) it is intended to mean "A or B or both". When the applicants intend to indicate "only A or B but not both" then the phrase "only A or B but not both" will be used. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is used herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be used.

What is claimed is:

1. A non-transitory computer-readable medium storing computer-executable instructions that when executed by a computer cause the computer to perform a method, the method comprising:
   receiving, from a patient device, a risk notification that a patient is at increased risk to experience an adverse event, where the risk notification includes a threshold condition;
   in response to receiving the risk notification and prior to the threshold condition being met, sending the risk notification to a caregiver device;
   in response to receiving, from the patient device, a clearance notification indicating that threshold condition has not been met and the patient is no longer at the increased risk, sending the clearance notification to the caregiver device; and
   in response to determining that the threshold condition has been met, generating an alert that indicates that the patient is experiencing the adverse event, and sending the alert to the caregiver device.

2. The non-transitory computer-readable medium of claim 1, where the alert includes at least one response option, where a response option provides a mode to respond to the alert.

3. The non-transitory computer-readable medium of claim 2, where the at least one response option includes a quick call option that allows the caregiver to initiate communication by selecting a button.

4. The non-transitory computer-readable medium of claim 1, where the alert is repeated a predetermined number of times when a response option is not selected.

5. The non-transitory computer-readable medium of claim 1, where the risk notification further includes a location of the patient and a description of the activity that the patient is participating in.

6. The non-transitory computer-readable medium of claim 1, where the threshold condition is a time interval.

7. The non-transitory computer-readable medium of claim 1, where the method further comprises:
   after generating the alert, receiving, from the patient device, the clearance notification; and
   clearing the alert.

8. The non-transitory computer-readable medium of claim 1, where the risk notification is received through a push notification service or short message service.

9. A non-transitory computer-readable medium storing computer-executable instructions that when executed by a computer cause the computer to perform a method, the method comprising:
   receiving, from a patient device, a risk notification that indicates that a patient is at increased risk to experience an adverse event, and where the risk notification includes a time interval;
   selecting a first caregiver device;
   sending the risk notification to the first caregiver device;
   receiving a first availability response, from the first caregiver device, that indicates that a first caregiver in possession of the first caregiver device will be available during the time interval;
   in response to receiving a clearance notification from the patient device prior to the time period elapsing, sending the clearance notification to the first caregiver device, where the clearance notification indicates that the patient is no longer at the increased risk to experience the adverse event;
   in response to determining that the time interval has elapsed without receipt of a clearance notification from the patient device, sending an alert to the first caregiver device, where the alert indicates that the patient is experiencing the adverse event.

10. The non-transitory computer-readable medium of claim 9, the method further comprising not sending the alert to the first caregiver device when the first availability response indicates that the first caregiver is not available during the time interval.

11. The non-transitory computer-readable medium of claim 10, where in response to receiving the first availability response that indicates that the first caregiver is not available during the time interval, the method further includes:
   selecting a second caregiver device;
   sending the risk notification to the second caregiver device;
   receiving a second availability response, from the second caregiver device, that indicates whether that a second caregiver in possession of the first caregiver device will be available during the time interval;
   determining that the time interval has elapsed without receipt of a clearance notification from the patient device; and sending an alert to the second caregiver device based, at least in part, on the second availability response, where the alert indicates that the patient is experiencing the adverse event.

12. The non-transitory computer-readable medium of claim 9, where the method further comprises
providing a group of caregivers selected from a social networking website; and
where the first caregiver is a member of the group of caregivers.

13. The non-transitory computer-readable medium of claim 9, where the method further comprises:
sending the alert to emergency services.

14. A system, the system comprising:
a risk notification logic configured to
receive, from a patient device, a risk notification that a patient in possession of the patient device is at increased risk to experience an adverse event, where the risk notification includes a threshold condition; and
send the risk notification to a caregiver device prior to the threshold condition being met;
a threshold logic configured to, in response to the risk notification:
monitor the threshold condition and a clearance condition and
when the threshold condition has been met; generate an alert that indicates that the patient is experiencing the adverse event; and
when the threshold condition has not been met and the clearance condition is met, send a clearance notification to the caregiver device that indicates that the patient is no longer at the increased risk; and
an alert logic configured to send the alert to the caregiver device.

15. The system of claim 14, where the threshold condition is a predetermined maximum heart rate, a minimum medication amount, a maximum foot-speed, a location boundary, or a temperature range of the patient.

16. The system of claim 15, where the threshold logic evaluates the threshold condition using alert threshold data received from a mobile device associated with the patient.

17. The system of claim 14, where the threshold logic is further configured to
after generating the alert, receive a clearance notification from the patient; and
in response to the clearance notification, clearing the alert.

18. The system of claim 14, where the system is implemented in an application on a mobile device.

* * * * *

UNITED STATES PATENT AND TRADEMARK OFFICE
CERTIFICATE OF CORRECTION

PATENT NO.        : 9,092,555 B2
APPLICATION NO.   : 13/955098
DATED             : July 28, 2015
INVENTOR(S)       : Gunaratnam et al.

Page 1 of 1

It is certified that error appears in the above-identified patent and that said Letters Patent is hereby corrected as shown below:

In the specification,

In column 9, line 49, delete "i/o" and insert -- I/O --, therefor.

In column 9, line 57, before "interfaces" delete "i/o" and insert -- I/O --, therefor.

In column 9, line 57, before "ports" delete "i/o" and insert -- I/O --, therefor.

In the claims,

In column 12, line 39, in claim 9, delete "device" and insert -- device, --, therefor.

In column 14, line 1, in claim 14, delete "met;" and insert -- met, --, therefor.

Signed and Sealed this
Twenty-fourth Day of May, 2016

Michelle K. Lee
*Director of the United States Patent and Trademark Office*